US009757499B2

(12) United States Patent
Langrana et al.

(10) Patent No.: US 9,757,499 B2
(45) Date of Patent: Sep. 12, 2017

(54) BIOMATERIAL AND METHODS OF USE THEREOF FOR THE PREVENTION OF POST-OPERATIVE ADHESIONS

(71) Applicant: RUTGERS, THE STATE UNIVERSITY OF NEW JERSEY, New Brunswick, NJ (US)

(72) Inventors: Noshir Langrana, West Windsor, NJ (US); Devendra Verma, Rourkela (IN); Michelle Previtera, Green Brook, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 14/569,199

(22) Filed: Dec. 12, 2014

(65) Prior Publication Data
US 2015/0098970 A1 Apr. 9, 2015

Related U.S. Application Data

(63) Continuation of application No. PCT/US2013/045403, filed on Jun. 12, 2013.

(60) Provisional application No. 61/658,647, filed on Jun. 12, 2012.

(51) Int. Cl.
*A61K 31/722* (2006.01)
*A61K 9/00* (2006.01)
*A61P 41/00* (2006.01)
*A61L 31/04* (2006.01)
*C08B 37/00* (2006.01)
*C08J 5/18* (2006.01)
*C08L 5/00* (2006.01)
*C08L 5/08* (2006.01)

(52) U.S. Cl.
CPC ........ *A61L 31/042* (2013.01); *C08B 37/0045* (2013.01); *C08J 5/18* (2013.01); *C08L 5/00* (2013.01); *C08L 5/08* (2013.01); *C08J 2305/00* (2013.01); *C08J 2305/08* (2013.01)

(58) Field of Classification Search
None
See application file for complete search history.

(56) References Cited

U.S. PATENT DOCUMENTS 5,356,883 A * 10/1994 Kuo ..................... A61K 9/0014
424/488
5,958,443 A * 9/1999 Viegas ................. A61F 9/00819
424/427
5,962,006 A * 10/1999 Southard ................ A61L 31/06
424/400
2002/0001609 A1 * 1/2002 Calhoun ............... A61B 17/70
424/426
2003/0087111 A1 * 5/2003 Hubbell ................. A61L 27/34
428/457
2005/0095275 A1 * 5/2005 Zhu .................... A61F 13/00063
424/445
2010/0247599 A1 * 9/2010 Krohne ............ A61K 47/48315
424/423

OTHER PUBLICATIONS

Westwood et al., "The characterisation of polygalacturonic acid-based layer-by-layer deposited films using a quartz crystal microbalance with dissipation monitoring, a dual polarization interferometer and a Fourier-transform infrared spectrometer in attenuated total reflectance mode", Soft Matter, 6, 5502-5513, 2010.*
Verma, "Polyelectrolyte Complex Membranes for Prevention of Post-Surgical Adhesions in Neurosurgery", Annals of Biomedical Engineering, vol. 40, No. 9, published online Apr. 13, 2012.*
Khanna, "In Situ Swelling Behavior of Chitosan-Polygalacturonic Acid/Hydroxyapatite Nanocomposites in Cell Culture Media", International Journal of Polymer Science, vol. 2010, Article ID 175264, 12 pages, published Jan. 2010.*
Arguelles-Monal, "Conductimetric study of the interpolyelectrolyte reaction between chitosan and polygalacturonic acid", Polymer 41, 2373-2378, 2000.*
Verma et al., Polyelectrolyte-complex nanostructured fibrous scaffolds for tissue engineering, Materials Science and Engineering: C, 2009, 2079-2084, 29(7).
Brodbeck et al., Biomaterial surface chemistry dictates adherent monocyte/macrophage cytokine expression in vitro, Cytokine, 2002, 311-9, 8(6).
Chen et al., Microstructure formation and property of chitosan-poly(acrylic acid) nanoparticles prepared by macromolecular complex, Macromol Biosci., 2005, 993-1000, 5(10).
Hamman et al., Chitosan Based Polyelectrolyte Complexes as Potential Carrier Materials in Drug Delivery Systems, Mar. Drugs, 2010, 1305-1322, 8(4).
Ishihara et al., Selective adhesion of platelets on a polyion complex composed of phospholipid polymers containing sulfonate groups and quarternary ammonium groups, J Biomed Mater Res., 1994, 1347-55, 28(11).
Ito et al., Controlled adhesion of human lymphocytes on electrically charged polymer surface having phosphorylcholine moiety, Science and Technology of Advanced Materials, 2003, 99-104, 4.
Rosso et al., New polyelectrolyte hydrogels for biomedical applications, Materials Science and Engineering: C, 2003, 371-376, 23.
Schatz et al., Formation and properties of positively charged colloids based on polyelectrolyte complexes of biopolymers, Langmuir, 2004, 7766-78, 20(18).

* cited by examiner

*Primary Examiner* — Robert T Crow
*Assistant Examiner* — John P Nguyen
(74) *Attorney, Agent, or Firm* — Kathleen D. Rigaut; Dann, Dorfman, Herrell & Skillman

(57) ABSTRACT

Biofunctional films and methods of use thereof for the prevention of post-operative adhesions are disclosed.

15 Claims, 3 Drawing Sheets

| Features | Interceed | Seprafilm | Our Technology |
|---|---|---|---|
| Biodegradation | 3-10 days | 2 weeks | 1-2 weeks |
| Physical Barrier | ✓ | ✓ | ✓ |
| Anti-adhesion (cells) | ✗ | ✗ | ✓ |
| Drug delivery | ✗ | ✗ | ✓ |
| Anti-inflammatory | ✗ | ✗ | ✓ |
| Laparoscopic Application | ✗ | ✗ | ✓ |

Figure 5

BIOMATERIAL AND METHODS OF USE THEREOF FOR THE PREVENTION OF POST-OPERATIVE ADHESIONS

This application is a §365 application of PCT/US2013/045403 filed Jun. 12, 2013, which in turn claims priority to U.S. Provisional Application No. 61/658,647 filed Jun. 12, 2012, the entire contents being incorporated herein by reference as though set forth in full.

FIELD OF THE INVENTION

The present invention relates to the fields of biomaterials and prevention of post-operative complications.

BACKGROUND OF THE INVENTION

Several publications and patent documents are cited throughout the specification in order to describe the state of the art to which this invention pertains. Each of these citations is incorporated herein by reference as though set forth in full.

Adhesions can occur following virtually all types of surgeries. Post-surgery trauma leads to inflammation which is a normal part of the healing process, but inflammation also encourages fibrous bands of scar tissue to develop, which can lead to adhesions. In addition to pain and bodily complications, adhesions lead to increased medical expenses. Costs include subsequent surgeries to remove or separate adhesions, doctor visits, pain medication and compensation for lost work time. Also, if a patient were to have a subsequent operation in the same surgical site, such operation can be complicated by existing adhesions. Surgeons have to spend a considerable amount of time removing the adhesions before a new procedure can begin. This may also prolong the patient's recovery time and increases the risk and cost of the surgery.

One of the procedures to reduce adhesion formation is to insert a physical barrier between potential adhesion forming tissue surfaces. INTERCEED® (Ethicon-brand absorbable adhesion barrier) and SEPRAFILM® (Genzyme-brand absorbable adhesion barrier) are the two FDA approved barrier devices available in United States. The success rates for INTERCEED® and SEPRAFILM® are 50% and 48% respectively. INTERCEED® is effective only in absence of blood contamination. SEPRAFILM® has low mechanical properties, is brittle and is difficult to handle. The success rates of these anti-adhesive barriers are still low and there is a need for development of more effective biomaterial, which can significantly reduce adhesions.

SUMMARY OF THE INVENTION

In accordance with the present invention a method of preventing post-surgical adhesions in a patient in need thereof is disclosed. An exemplary method entails providing a complex of polyelectrolytes (PEC), the complex forming a film. The resulting film is introduced into a surgical site, where the film is effective to separate healing tissues and is maintained post-operatively at said surgical site for a period of at least about seven days. In a particularly preferred embodiment, the PEC complex comprises chitosan and polygalacturonic acid present in a 40:60 ratio and exhibits anti-inflammatory properties. Also encompassed by the invention is a film comprising chitosan and polygalacturonic acid present in a 40:60 ratio. In one embodiment, the film has a thickness between 75-250 microns. In a preferred embodiment, the film has a thickness of about 180 microns. The invention also comprises films having three components, including without limitation, a complex of polyelectrolytes, comprising about 30-40% chitosan and about 55% galacturonic acid and about 5% pectin and having a thickness between 150 and 200 microns. In yet another aspect, a biofilm for use in the methods disclosed herein is composed of a complex of polyelectrolytes, the complex comprising about 40% chitosan, about 40% polygalacturonic acid and about 20% dextran sulphate and having a thickness of about 150-200 microns.

BRIEF DESCRIPTION OF THE DRAWINGS

FIG. 5 is a table showing a comparison of the inventive film of the invention to other films in the art.

DETAILED DESCRIPTION OF THE INVENTION

Figure 1:
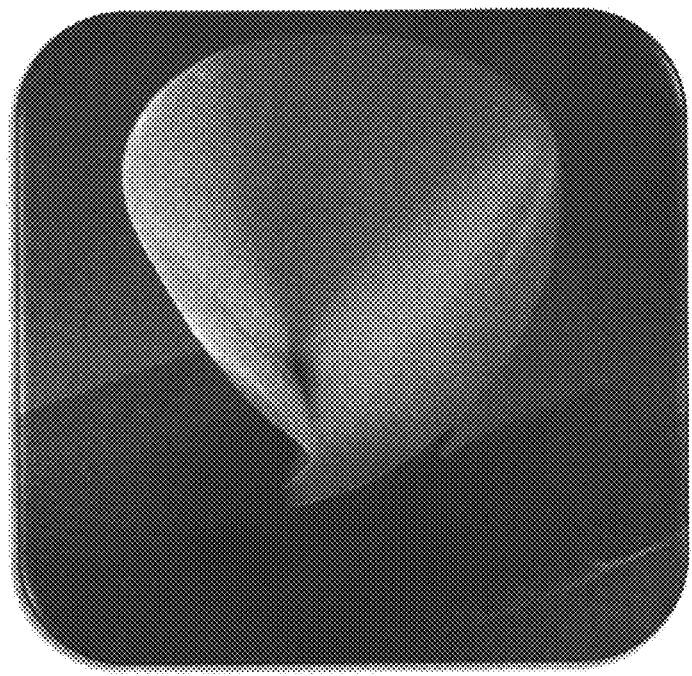
FIG. 1 is a photograph of the biodegradable and biocompatible film of the invention.

PECs primarily consist of at least two oppositely charged polymers. Polyelectrolyte complex biomaterials, especially polysaccharide based, have a potential for wound healing, drug delivery and tissue-engineering applications [1]. PEC materials can be formed using different methods. Among the most common method is co-acervation of polymer solutions. In this method, one of the polymer solutions is added drop-wise to its complementary charged polymer solution under rapid agitation. This results in formation of a nano-colloidal PEC suspension in unreacted polymer mixer [2]. The driving force for such complexation is entropy and strong electrostatic attraction between the complementary charged polymers. The parameters that affect the structure of the PEC particles are pH, ionic strength, and polymer mixing order [3].

By comparison with current products, polyelectrolyte complex (PEC) based films provide the benefits of ease of handling when wet or dry and are strong enough to hold sutures. These films not only act as a physical barrier but also inhibit adhesion by electrostatic interactions. Furthermore, since the product is based on chitosan, it offers the additional physiological properties of homeostasis and accelerated healing of the surgical wound. Polygalacturonic acid is another biocompatible and biodegradable polymer, which provides negative surface charge to PEC and hence prevents cell adhesion. Another important aspect of these films is their anti-inflammatory property. Up-regulation of inflammation after trauma has been shown to be critical factor in adhesion formation. The anti-inflammatory characteristics of chitosan/PgA films provide an additional mechanism to prevent post-surgical adhesions.

Chitosan and polygalacturonic acid form polyelectrolyte complexes in solution. By varying their proportion, e.g., use of between 30%, 40%, 50%, 60% or 70% chitosan with proportional PgA, films with specific charge densities have been created. These PEC films have adequate mechanical strength and residence time inside the body and are useful to prevent complications from surgical intervention. PgA is a product of pectin degradation. Pectin is a plant polysaccharide primarily obtained from edible plants. Pectin contains poly(d-galacturonic acid) bonded via glycosidic linkage and. Pectin also contains neutral sugars, which are either inserted in or attached to the main chains. Since PgA and Pectin share chemical similarity, in certain embodiments of this invention, PgA can be replaced by pectin. The molecular weights of chitosan and PGA polymers are design parameters. We can fabricate films with high to low molecular weights of polymers based on the film properties desired. Technically any water soluble polsaccharide or protein can be added to chitosan/polygalacturonic acid films. These polymers include for example alginate, dextran sulfate, collagen, gelatin, chitin, polylysine, heparin, hyaluronic acid, methoxy cellulose, and oxidized regenerated cellulose. The polymers can be added individually or in combination to alter the properties.

Other useful polymers can be employed to create the films of the invention. These include, without limitation, 1. Pectin/chitosan/hydroxypropyl methylcellulose (Macleod G S, et al. Int J Pharm. 1999; 187(2):251-7) 2. Pectin/Chitosan/Alginate (Yu C Y et al. Colloids and Surfaces B: Biointerfaces. 2009; 68(2):245-9) 3. Pectin/Chitosan/Gelatin (Li J, et al. Journal of Biomedical Materials Research Part B: Applied Biomaterials. 2010; 95(2):308-19) and 4. Pectin/Chitosan/Poly-l-lysine (Marudova M, et al. Carbohydr Res. 2005; 340(13):2144-9).

Many studies have shown that polymers with negatively charged functional groups, such as carboxylate and sulfate, have an inhibitory effect on adhesions of macrophages [4], lymphocytes [5], platelets [6] and fibroblasts [7]. Polyelectrolyte complexes (PEC) primarily consist of at least two oppositely charged polymers. By keeping the concentration of polyanions (PgA) higher than polycations (chitosan), a film with an overall negative charge can be created. Chitosan/PgA films with lower than 50:50 ratios, are effective in achieving non-adhesive properties. Additional polymers useful for the practice of the invention include three material composites, such as chitosan-PGA-pectin and Chitosan-PGA dextran sulfate. These three material composites should possess improved properties such as mild stickiness. In these composites chitosan will be kept at approximately 40%. Pectin and Dextran sulphate will range from 5 to 20% and the remainder will be PGA. In a preferred embodiment, a chitosan (40%)-PGA (55%)-Pectin (5%) composite can be prepared. In yet another embodiment, a chitosan (40%)-PGA (40%)-Dextran sulphate (20%) can be prepared.

Adhesion Prevention or Inhibition

This invention is also directed to methods of preparing degradable gels and films which can be used as surgical aids to prevent adhesions and accretions of body tissues.

In many instances of practical surgery, it is highly desirable to have a simple means and method for preventing direct contact between tissues and for maintaining this contact-inhibiting effect also during a post-operative or healing period. The length of the period will vary according to the actual type of surgery involved. Examples of surgical procedures in which the biocompatible gels, and films of this invention may be used include, but are not limited to, operations performed in abdominal regions where it is important to prevent adhesions of the intestine or the mesentery; operations performed in the urogenital apparatus where it is important to ward off adverse effects on the ureter and bladder, and on the functioning of the oviduct and uterus; and nerve surgery operations where it is important to minimize the development of granulation tissue. In surgery involving tendons there is generally a tendency towards adhesion between the tendon and the surrounding sheath or other surrounding tissue during the immobilization period following the operation. Attempts to solve this problem by using various kinds of sutures and by means of passive movements of the tendon during the healing process have been unsuccessful.

In opthalmological surgery it is often desirable to have degradable implants at one's disposal which are to be applied in the angle of the anterior chamber of the eye for the purpose of preventing synechiae between the cornea and the iris; this applies especially in cases of reconstructions after severe damaging events. Moreover, degradable or permanent implants are often desirable for preventing adhesion after glaucoma surgery and strabismus surgery.

In one particular type of articular surgery, silicone plates are surgically introduced in order to prevent accretions of cartilaginous tissue. Engkvist et al., Scand J. Plast. Reconstr. Surg. 14: 71-87 (1980). After 12 to 16 weeks, however, it is necessary to surgically remove the implant. Thus, the techniques presently available necessitate removal of the inserted material after a suitable period of time in all cases where this material has to be of a rigid type for the sake of securing a high degree of mechanical stability. In other cases, where mechanical stability is not a major factor, it has been customary to use non-crosslinked dextran or hyaluronic acid. But even if a substance of such high viscosity as hyaluronic acid is used for application to contact surfaces, the protection period obtained is too short to be satisfactory.

The gel, or film is introduced between or among the tissues of a surgical site, either during surgery or post-operatively, to separate the healing tissues or to prevent post-operative adhesion between the healing tissues. The gels and films of this invention are particularly advantageous because they will diffuse or be degraded after a desired period of time. However, it must remain in place and prevent tissue contact for a long enough time so that when the gel or film finally disperses or degrades and the tissues do come into contact, they will no longer have a tendency to adhere. Preferably, the tissues should be separated for a period of at least about 7 days post-operatively.

The rate at which the gel, or film diffuses will depend primarily on the nature of the composition (including the nature of the polymers in the polyelectrolyte complex). The amounts of these polymers can be adjusted to make the film thicker, more or less soluble and more or less rigid. The rate of diffusion required will vary according to the type of surgery involved. Those skilled in the art will know, or will be able to ascertain with no more than routine experimentation, the appropriate combination of insolubility, density and chemistry that will yield a gel, or a film having the desired rate of diffusion for a given situation.

Drug Delivery

The gels and films of the invention can also be used as vehicles for delivering pharmaceutically-active substances to a desired site in the body of a mammal. A pharmaceutically-active substance can be chosen which covalently bonds to the gel or film of the invention to form a drug delivery system with controlled release. Alternatively, a pharmaceutically-active substance can be chosen which non-covalently interacts with the film. In both cases, the drug delivery system is then injected or implanted at the locus where delivery is desired. Suitable pharmaceutically-active substances include growth factors, enzymes, therapeutic drugs, biopolymers, and biologically compatible synthetic polymers.

Delivery is also related to the degradation of the gel or film as a result of numerous metabolic processes taking place in vivo. Other types of drug delivery systems according to the present invention include those in which a drug is dispersed within the gel or film. As used herein, the term "dispersed" shall refer to ionic and hydrophobic interactions between the drug and the film.

The following example is provided to illustrate certain embodiments of the invention. It is not intended to limit the invention in any way.

Materials

Chitosan and polygalacturonic acid were obtained from Sigma-Aldrich chemicals. All chemicals and polymers are used as obtained.

Preparation of Complex Chitosan and Polygalacturonic Acid (PGA) Polymers

Chitosan solution (1% w/v) was prepared by dissolving 0.3 g chitosan in 30 mL of deionized water containing 1 ml of 1N HCl acid. PgA solution (1% w/v) was prepared by dissolving 0.3 g PgA in 30 mL of deionized water containing 1 ml of 1N NaOH. These two solutions were then mixed together by adding chitosan solution drop-wise to PgA solution. The mixed solution was sonicated and air dried in a petridish to make the membranes.

Spot Assay

Circular coatings of PECs were created at the center of each tissue culture well in 24-well plates using 1 μL of the solution. The spots were allowed to air dry to attach to tissue culture plates. The size of spots were approximately 1 mm in diameter after drying. GFP fibroblast cells were seeded at a density of $5 \times 10^3$ cells per well. Images were taken after 5 day in culture.

LPS Assay

A petri dish was coated with the film disclosed herein. Peritoneum macrophages treated with Lipopolysaccharides (LPS), were seeded on non-coated and coated plates and the level of TNF-α secreted determined using ELISA.

Experimental Model of Adhesion

Two ischemic buttons were created in peritoneal cavity after which a 2 inch diameter film was placed in the peritoneal cavity. The incision was closed with sutures and the wound evaluated after one week.

Example 1

Biofunctional Film for Prevention of Post-Operative Adhesions

We have developed PECs comprising complex chitosan and polygalacturonic acid (PGA)polymers. In a preferred embodiment the polymers form a thin sheet (or film) 0.05 mm thick and the size can be as large as 150 mm diameter. We can vary the thickness of the film by altering the ratios of the components utilized to make the polymers. Thickness can vary between 75-250 microns, preferably between 100-200 microns and more preferably between 160 and 180 microns. Thickness of the film is directly related to longevity in vivo.

Utilizing a chitosan—PGA ratio of 40:60 provided favorable results in experimental assays. FIG. 1 shows a photograph of a film of the invention which is strong and flexible. The film exhibits several desirable properties. It is comprised of non-toxic natural material. It is biodegradable. It also possesses anti-adhesive and anti-inflammatory properties.

Figure 2:
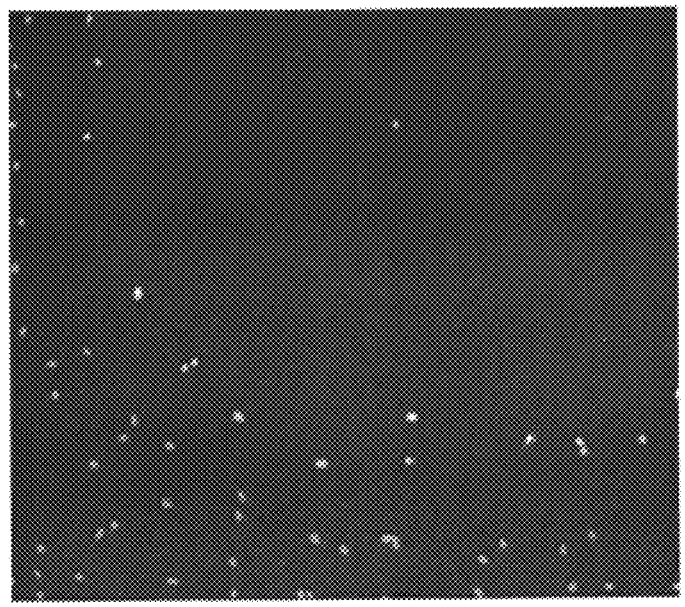
FIG. 2 is photograph showing that the inventive composition inhibits fibroblast adhesion

FIG. 2 is a photograph demonstrating anti-adhesive effects of the film to the fibroblast cells. The film inhibited adhesion of fibroblast cells.

Figure 3:
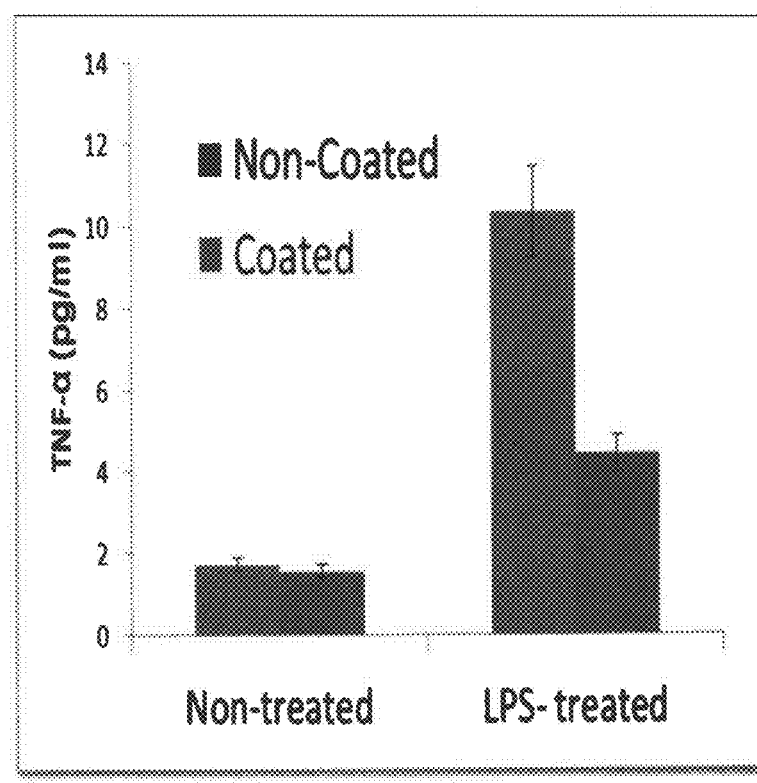
FIG. 3 is graph showing that the inventive film possesses anti-inflammatory properties.

FIG. 3 is a graph demonstrating the anti-inflammatory effects of the film in an LPS assay. Secretion of TNF-α in LPS treated macrophages was markedly decreased in the presence of the film.

Figure 4:
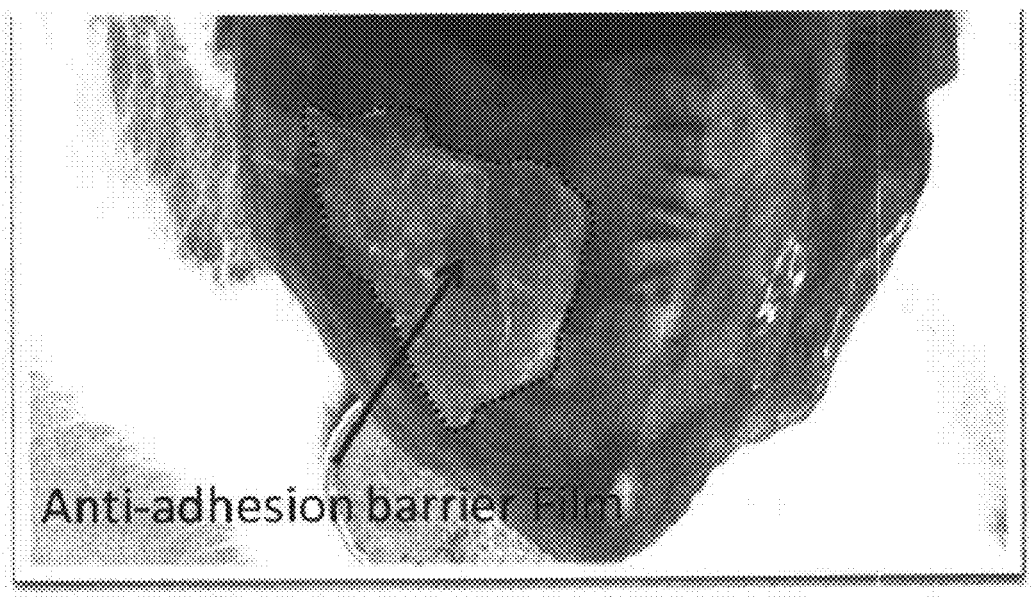
FIG. 4 is a photograph showing the film prevents adhesion formation.

The results of an in vivo model of adhesion are shown in FIG. 4. After ischemic buttons were created in the peritoneal cavity, the film was applied and the wound allowed to heal for seven days. The results revealed that the film prevented adhesion formation, was free of fibrotic encapsulation and was also partially degraded.

PEC films, particularly, films of chitosan-polygalacturonic and Chitosan have shown to be a barrier for adhesion prevention, because of following reasons: These films can act as a physical barrier. The negatively charged surface can electrostatically inhibit adhesion of different cell types and also provided anti-inflammatory effects. Notably, the thickness of the film dictates the longevity of the filmin vivo. For example 100 micron film degraded within a week, whereas 180 micron film remained intact and we were able to remove them from test subjects intact. The initial stiffness and strength of 180 micron film gives rise to a slower rate of degradation. FIG. 5 summarizes the superior and beneficial features of the inventive film disclosed herein.

REFERENCES

1. Hamman, J H. Chitosan based polyelectrolyte complexes as potential carrier materials in drug delivery systems. Mar. Drugs 8:1305-1322, 2010.
2. Schatz C, Lucas J M, Viton C, Domard A, Pichot C, and Delair T. Formation and properties of positively charged colloids based on polyelectrolyte complexes of biopolymers. Langmuir 20:7766-7778, 2004.
3. Chen Q, Hu Y, Chen Y, Jiang X, and Yang Y. Microstructure formation and property of chitosan-poly(acrylic acid) nanoparticles prepared by macromolecular complex. Macromol. Biosci. 5:993-1000, 2005.
4. Brodbeck W, Nakayama Y, Matsuda T, Colton E, Ziats N, Anderson J. Biomaterial surface chemistry dictates adherent monocyte/macrophage cytokine expression in vitro. Cytokine 2002; 18:311-319.
5. Ito T, Iwasaki Y, Narita T, Akiyoshi K, Ishihara K. Controlled adhesion of human lymphocytes on electrically charged polymer surface having phosphorylcholine moiety. Science and Technology of Advanced Materials 2003; 4:99-104.
6. Ishihara K, Inoue H, Kurita K, Nakabayashi N. Selective adhesion of platelets on a polyion complex composed of phospholipid polymers containing sulfonate groups and quarternary ammonium groups. J Biomed Mater Res 1994; 28:1347-1355.
7. Rosso F, Barbarisi A, Barbarisi M, Petillo O, Margarucci S, Calarco A, Peluso G. New polyelectrolyte hydrogels for biomedical applications. Materials Science and Engineering: C 2003; 23:371-376.

While certain preferred embodiments of the present invention have been described and specifically exemplified above, it is not intended that the invention be limited to such embodiments. Various modifications may be made to the invention without departing from the scope and spirit thereof as set forth in the following claims.

What is claimed is:

1. A method of preventing post-surgical adhesions in a patient in need thereof comprising: providing a complex of polyeletrolytes (PEC), comprising a mixture of polycationic chitosan and polyanionic polygalacturonic acid (PGA) in the form of a dry film;
   introducing said dry film into a surgical site, said dry film being effective to separate healing tissues, and maintaining said dry film post-operatively at said surgical site for a period of at least seven days.

2. The method of claim 1, wherein said dry film comprises a mixture of chitosan and polygalacturonic acid in a ratio of 1:1 by weight, or a ratio in which the weight percent of polyanionic PGA exceeds the weight percent of polycationic chitosan in said dry film, thereby imparting an overall negative charge to said film.

3. The method of claim 2, wherein said dry film comprises a mixture of chitosan and polygalacturonic acids in a ratio of 40:60 by weight.

4. The method of claim 3 wherein said dry film has a thickness between 75-250 microns.

5. The method of claim 4, wherein said dry film has a thickness of about 100 microns.

6. The method of claim 4, wherein said dry film has a thickness of about 180 microns.

7. The method of claim 1, wherein said complex of polyeletrolytes exhibits anti-inflammatory properties.

8. The method of claim 1, wherein the surgical site is produced from cardiosurgery, articular surgery, abdominal surgery, thoracic surgery, surgery in the urogenital region, nerve surgery, tendon surgery, laparascopic surgery, pelvic surgery, oncological surgery, sinus and craniofacial surgery, ENT surgery, ophthalmological surgery, or a procedure involving spinal dura repair.

9. The method of claim 1, wherein the dry film is preformed prior to contacting the surgical site.

10. The method of claim 2, wherein said complex of polyeletrolytes further comprises pectin or dextran sulphate.

11. The method of claim 10, wherein said complex of polyeletrolytes comprises chitosan-polygalacturonic acid-pectin.

12. The method of claim 11, wherein said complex of polyeletrolytes comprises about 40% chitosan, about 55% polygalacturonic acid and about 5% pectin.

13. The method of claim 10, wherein said complex of polyeletrolytes comprises chitosan-galacturonic acid-dextran sulphate.

14. The method of claim 13, wherein said complex of polyeletrolytes comprises about 40% chitosan, about 40% galacturonic acid and about 20% dextran sulphate.

15. A method of preventing post-surgical adhesions in a patient in need thereof comprising: providing a complex of polyeletrolytes (PEC), comprising a mixture of polycationic chitosan and polyanionic polygalacturonic acid (PGA);
   introducing said mixture into said surgical, said mixture forming a film at said site, said film being effective to separate healing tissues, and maintaining said film post-operatively at said surgical site for a period of at least seven days.

* * * * *